(12) United States Patent
Bastide et al.

(10) Patent No.: US 11,154,221 B2
(45) Date of Patent: Oct. 26, 2021

(54) DIAGNOSING CHANGES IN GAIT BASED ON FLEXIBILITY MONITORING

(71) Applicant: International Business Machines Corporation, Armonk, NY (US)

(72) Inventors: Paul R. Bastide, Boxford, MA (US); Jonathan Dunne, Dungarvan (IE); Liam S. Harpur, Skerries (IE); Robert Loredo, North Miami Beach, FL (US)

(73) Assignee: International Business Machines Corporation, Armonk, NY (US)

( * ) Notice: Subject to any disclaimer, the term of this patent is extended or adjusted under 35 U.S.C. 154(b) by 465 days.

(21) Appl. No.: 15/933,858

(22) Filed: Mar. 23, 2018

(65) Prior Publication Data

US 2019/0290168 A1 Sep. 26, 2019

(51) Int. Cl.
*A61B 5/11* (2006.01)
*A63B 24/00* (2006.01)

(52) U.S. Cl.
CPC .......... *A61B 5/112* (2013.01); *A63B 24/0062* (2013.01); *A63B 2024/0065* (2013.01); *A63B 2024/0068* (2013.01)

(58) Field of Classification Search
CPC ..... A61B 5/112; A61B 5/1107; A61B 5/1114; A61B 5/1116; A61B 5/1121; A61B 5/1122; A61B 5/1123; A61B 5/1126; A61B 5/1127; A61B 11/1036; A61B 5/1038; A61B 5/1071; A61B 24/0059–0087; A61B 2024/009–0096; A61B 2220/10; A61B 2220/13; A61B 2220/836; A61B 71/06–0697; A61M 2230/60; A61M 2230/605; A61M 2230/62; A61M 2230/625; A61M 2230/75;

(Continued)

(56) References Cited

U.S. PATENT DOCUMENTS 6,360,597 B1  3/2002  Hubbard
6,689,019 B2  2/2004  Ohrt et al.
7,462,134 B2  12/2008  Lull et al.

(Continued)

OTHER PUBLICATIONS

Song, Jinsup, et al. "Comprehensive Biomechanical Characterization of Feet in USMA Cadets: Comparison across Race, Gender, Arch Flexibility, and FootTypes." Gait & Posture, vol. 60, 2018, pp. 175-180., doi: 10.1016/j.gaitpost.2017.12.001. (Year: 2018).*

(Continued)

*Primary Examiner* — Matthew Kremer
*Assistant Examiner* — Samuel C Kim
(74) *Attorney, Agent, or Firm* — Will Stock; Edell, Shapiro & Finnan, LLC (57) ABSTRACT

Methods, systems, and computer program products are provided for measuring and analyzing muscle flexibility to infer a change in gait. Muscle flexibility measurements are obtained using at least one sensor of a device attached to a body of a user. A flexibility quotient is calculated based on the obtained muscle flexibility measurements, user information, a type of activity, a workout duration and baseline data. A change in flexibility based on the calculated flexibility quotient and a baseline flexibility quotient is determined. A change in gait is inferred based on the determined change in flexibility and is reported to the user.

20 Claims, 6 Drawing Sheets

(58) Field of Classification Search
CPC . A61M 2230/755; G16H 40/63; G16H 50/20; G16H 20/30
See application file for complete search history.

(56) References Cited

U.S. PATENT DOCUMENTS

| | | |
|---|---|---|
| 9,161,872 B2 | 10/2015 | Lee et al. |
| 9,351,900 B2 | 5/2016 | Walsh et al. |
| 2005/0033200 A1* | 2/2005 | Soehren ............... A61B 5/1123 600/595 |
| 2008/0146968 A1 | 6/2008 | Hanawaka et al. |
| 2009/0030350 A1 | 1/2009 | Yang et al. |
| 2011/0003665 A1* | 1/2011 | Burton .................. G04G 9/007 482/9 |
| 2013/0131555 A1 | 5/2013 | Hook et al. |
| 2013/0274904 A1* | 10/2013 | Coza .................. A63B 71/0619 700/91 |
| 2014/0062703 A1* | 3/2014 | Purks ................... A61B 5/1038 340/573.1 |
| 2014/0100494 A1 | 4/2014 | Sarkodie-Gyan et al. |
| 2015/0125832 A1 | 5/2015 | Tran |
| 2016/0143800 A1 | 5/2016 | Hyung et al. |
| 2016/0263433 A1 | 9/2016 | Wu |
| 2017/0095181 A1* | 4/2017 | Hauenstein .......... G01C 22/006 |
| 2017/0266501 A1* | 9/2017 | Sanders ................... G06N 3/04 |
| 2017/0354348 A1* | 12/2017 | Winter ................... A61B 5/112 |

OTHER PUBLICATIONS

Wearable Muscle Tension Sensors Know More Than What You Feel, http://www.medgadget.com/2008/07/wearable_muscle_tension_sensors_know_more_than_what_you_feel.html, Medgadget, LLC, retrieved from internet Mar. 2018, 7 pages.

Watson, An iPad app for gait analysis???, http://www.zflomotion.com/blog/bid/333446/Apps-for-gait-analysis, Sep. 18, 2014, 6 pages.

Gangemi, Out of the Gait: A Sock Doc Review of Running Gait, http://sock-doc.com/out-of-the-gait-a-sock-doc-review-of-running-gait/, retrieved from internet Mar. 2018, 7 pages.

* cited by examiner

DIAGNOSING CHANGES IN GAIT BASED ON FLEXIBILITY MONITORING

BACKGROUND

1. Technical Field

Present invention embodiments relate to methods, systems and computer program products for inferring changes in a gait of an individual, based on determining a difference in flexibility from a baseline.

2. Discussion of the Related Art

Jogging enthusiasts want their running shoes to be suited to their needs. Currently, a number of systems exist for measuring a runner's gait. Once the gait is known, a specific running shoe can be identified and purchased based on the gait. However, once a runner's gait is measured, the runner improperly assumes that his or her gait will remain constant during his or her lifetime. For example, sports professionals and people who run for leisure frequently incur injuries. Studies have shown that an individual's gait will change to compensate for a specific injury.

Current systems for measuring a gait of an individual use specific measuring apparatus, which can only be found in a sports lab or a high-end sport supply shop. Therefore, the individual must travel to the sports lab or the high-end sport supply shop in order to have his or her gait measured.

SUMMARY

According embodiments of the invention, a method, a system and a computer program product are provided for measuring and analyzing muscle flexibility to infer a change in gait. Muscle flexibility measurements may be obtained using at least one sensor of a device attached to a body of a user. A flexibility quotient is calculated based on the muscle flexibility measurements, user information, a type of activity, a workout duration and baseline data. A change is flexibility is determined based on the calculated flexibility quotient and a baseline flexibility quotient. The change in gait is inferred based on the determined change in flexibility. The inferred change in gait is reported to the user.

BRIEF DESCRIPTION OF THE DRAWINGS

Generally, like reference numerals in the various figures are utilized to designate like components.

DETAILED DESCRIPTION

In various embodiments, one or more baseline measurements may be made for an individual. The baseline measurements, or baseline data, may include, but not be limited to, age, activity, workout duration in minutes, a current gait, a pronation type, and muscle flexibility. The baseline data as well as other information may be fitted to a line using binary regression or other well-known techniques.

In some embodiments, the baseline data and the other information may be used to calculate a flexibility quotient. A formula for calculating the flexibility quotient may be of a form:

$$\ln\left(\frac{p}{1-p}\right) = C_0 + (C_1 \times \text{age}) + (C_2 \times \text{workout\_duration}) + (C_3 \times \text{muscle\_flexibility}),$$

where p is the flexibility quotient, age is an age of an individual, workout_duration is a time in minutes for a workout, and muscle_flexibility is a measurement of muscle flexibility, which may have an inclusive range between 0% and 100%. $C_0$, $C_1$, $C_2$ and $C_3$ may be constants derived by using binary regression. In other embodiments, additional parameters may be included in a formula for calculating the flexibility quotient. For example, if the formula is to additionally include an individual's weight, a type of activity, a current gait, and pronation, the formula may be of a form:

$$\ln\left(\frac{p}{1-p}\right) = C_0 + (C_1 \times \text{age}) + (C_2 \times \text{weight}) +$$
$$(C_3 \times \text{activity}) + (C_4 \times \text{workout\_duration}) +$$
$$(C_5 \times \text{gait}) + (C_6 \times \text{pronation}) + (C_6 \times \text{muscle\_flexibilty}).$$

In various embodiments, the flexibility quotient may have a value in a range from 0 to 1. Higher values of the flexibility quotient may indicate a loss in flexibility with respect to lower values of the flexibility quotient. According to various embodiments, the flexibility quotient can be used to infer or predict a likely change in gait from a known baseline and can be used to suggest a likely gate diagnosis based on increased or decreased muscle flexibility from a specific body part measurement.

Figure 1:
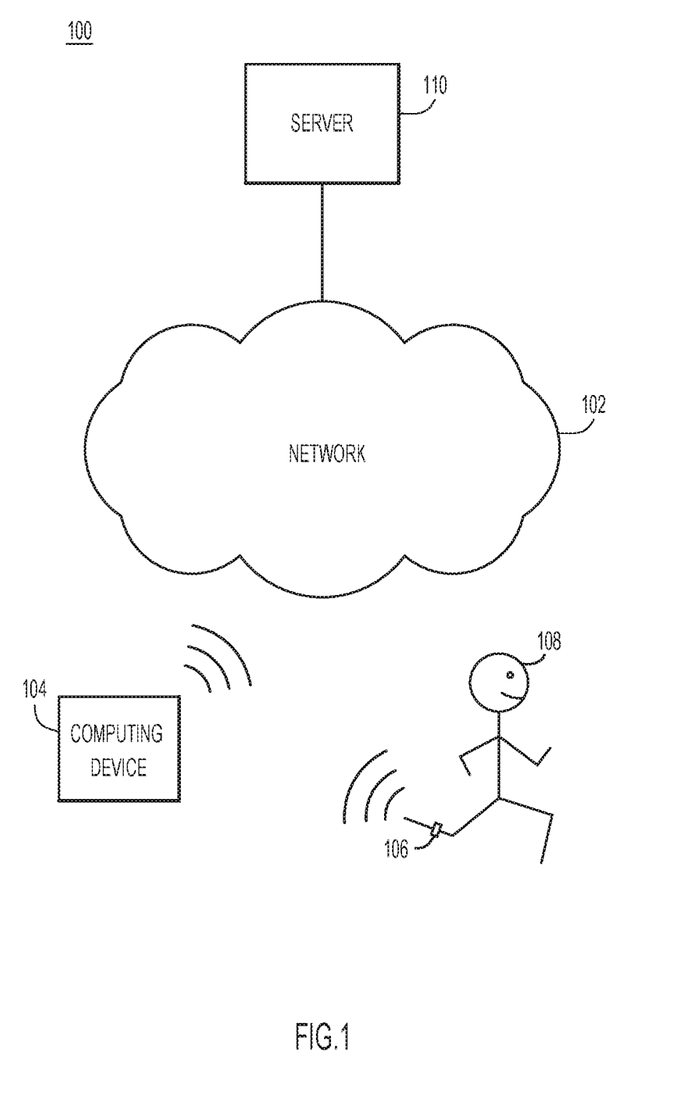
FIG. 1 illustrates an example environment in which various embodiments of the invention may operate.

FIG. 1 illustrates an example environment 100 in which various embodiments may operate. Example environment 100 includes a network 102 to which are connected, via a wired or wireless connection, a computing device 104 and a server 110.

Network 102 may be implemented by any number of any suitable communications media (e.g., wide area network (WAN), local area network (LAN), Internet, Intranet, etc.) or a combination of any of the suitable communications media. Network 102 may further include wired and/or wireless networks.

Computing device 104 may include a desktop computer, a laptop computer, a smartphone, or other type of computing device. Server 106 may include a single computer or may include multiple computers configured as a server farm. The one or more computers of server 106 may include a mainframe computer, a desktop computer, or other types of computers and may have access to one or more databases (not shown).

Alternatively, embodiments of the invention may be implemented by a standalone computing device 104 that may include, or have access to, the one or more databases. In a second alternative embodiment, a supplemental sensor device 106 may be attached to a body part of an individual 108. In some embodiments, the body part may be a lower leg, an upper leg, or another body part. Supplemental sensor device 106 may include at least one sensor (e.g., accelerometer) that measures a change in angle as individual 108 performs warmup stretching exercises and cooldown stretching exercises.

In embodiments that do not use supplemental sensor device 106, computing device 104 may be a small portable device including, but not limited to, a smart phone, which may be attached to a body part of the individual 108 via a strap or other attachment. The small portable device may include at least one sensor (e.g., accelerometer) that measures a change in angle as individual 108 performs warmup stretching exercises and cooldown stretching exercises.

Figure 2:
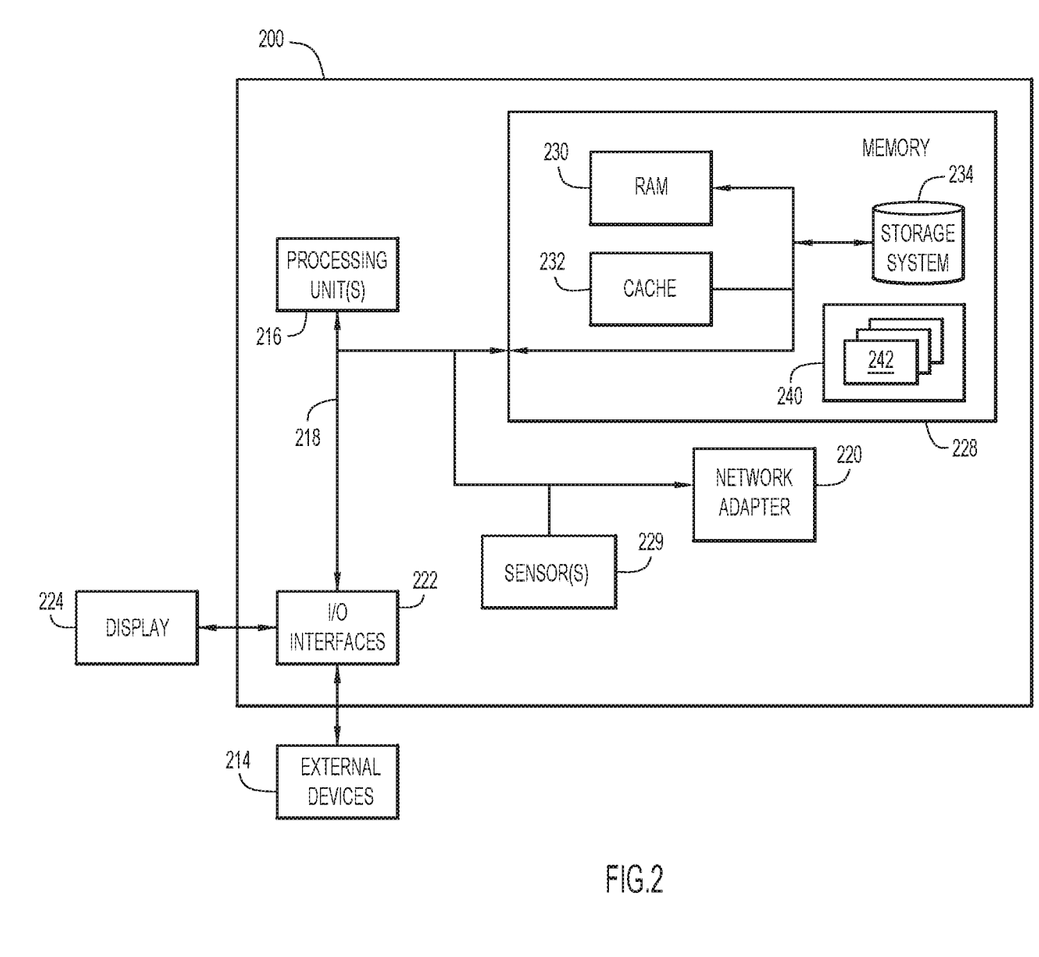
FIG. 2 illustrates an example computing system that may implement a computing device, a server or a supplemental sensing device according to embodiments of the invention.

Referring now to FIG. 2, a schematic of an example computing system 200 is shown. Computing system 200 may implement computing device 104, supplemental sensing device 106, and/or server 110. Computing system 200 is shown in a form of a general-purpose computing device. Components of computing system 200 may include, but are not limited to, one or more processors or processing units 216, a system memory 228, and a bus 218 that couples various system components including system memory 228 to one or more processing units 216.

Bus 218 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computing system 200 may include a variety of computer system readable media. Such media may be any available media that is accessible by computing system 200, and may include both volatile and non-volatile media, removable and non-removable media.

System memory 228 can include computer system readable media in the form of volatile memory, such as random access memory (RAM) 230 and/or cache memory 232. Computing system 200 may further include other removable/non-removable, volatile/non-volatile computer system storage media. By way of example only, storage system 234 can be provided for reading from and writing to a non-removable, non-volatile magnetic medium (not shown, which may include a "hard drive" or a Secure Digital (SD) card). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 218 by one or more data media interfaces. As will be further depicted and described below, memory 228 may include at least one program product having a set (e.g., at least one) of program modules that are configured to carry out the functions of embodiments of the invention.

Program/utility 240, having a set (at least one) of program modules 242, may be stored in memory 228 by way of example, and not limitation, as well as an operating system, one or more application programs, other program modules, and program data. Each of the operating system, the one or more application programs, the other program modules, and the program data or some combination thereof, may include an implementation of a networking environment. Program modules 242 generally carry out the functions and/or methodologies of embodiments of the invention as described herein.

Computing system 200 may also communicate with one or more external devices 214 such as a keyboard, a pointing device, one or more displays 224, one or more devices that enable a user to interact with computing system 200, and/or any devices (e.g., network card, modem, etc.) that enable computing system 200 to communicate with one or more other computing devices. Such communication can occur via Input/Output (I/O) interfaces 222. Still yet, computing system 200 can communicate with one or more networks such as a local area network (LAN), a general wide area network (WAN), and/or a public network (e.g., the Internet) via network adapter 220. As depicted, network adapter 220 communicates with the other components of computing system 200 via bus 218. Further, when implementing computing device 104 or supplemental sensing device 106, computing system 200 may include a sensor 229 connected to bus 218. It should be understood that, although not shown, other hardware and/or software components could be used in conjunction with computing system 200. Examples, include, but are not limited to: microcode, device drivers, redundant processing units, external disk drive arrays, RAID systems, tape drives, and data archival storage systems, etc.

Figure 3:
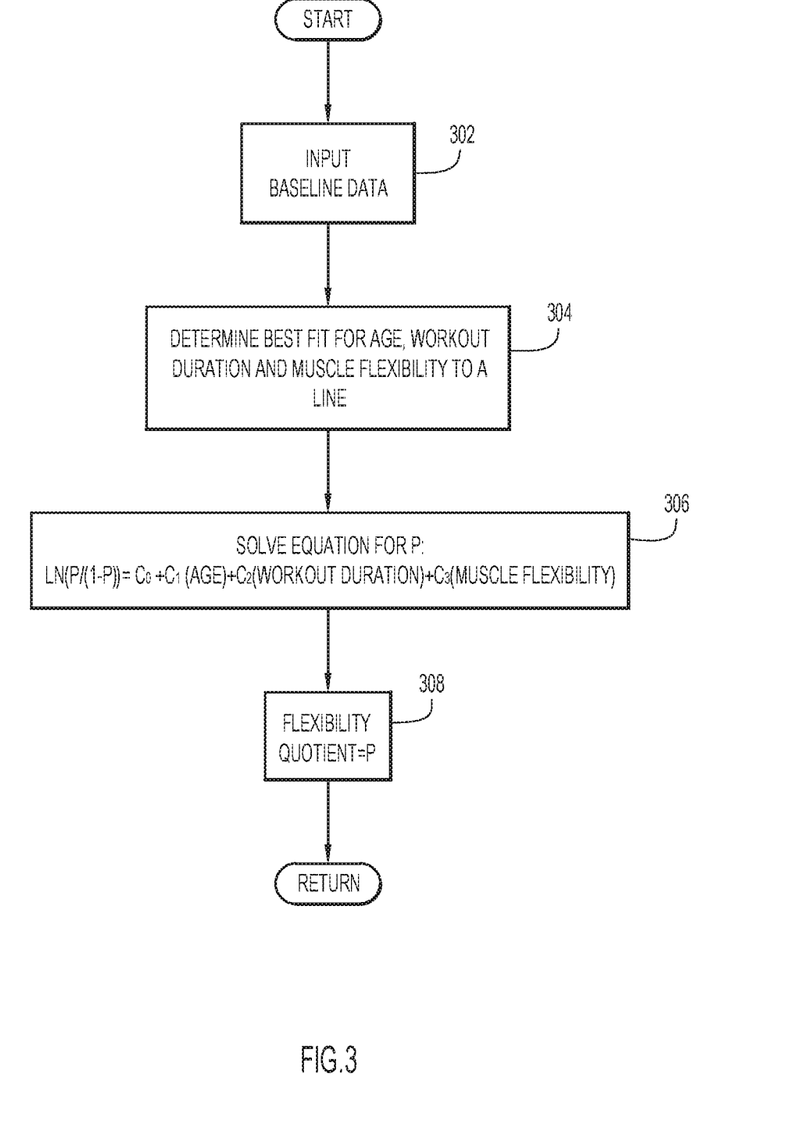
FIG. 3 is a flowchart illustrating a process for inputting baseline data and determining a baseline flexibility quotient according to embodiments of the invention.

FIG. 3 is a flowchart of an example process for inputting baseline data and calculating a baseline flexibility quotient. The process may begin with an individual inputting baseline data into a computing device such as, for example, computing device 104 (act 302). The baseline data may include an age of an individual, a weight of the individual, an activity, a current date, a workout duration in minutes, a pronation type, and muscle flexibility, which may be in a percentage in a range from 0% to 100%. The activity and the pronation type may each be enumerated to have a numeric value. For example, with respect to the activity, running may have a value of 1, cycling may have a value of 2, and walking may have a value of 3. With respect to pronation type, neutral may have a value of 1, under may have a value of 2, and over may have a value of 3.

Next, computing device 104 may determine, or estimate, a best fit Least-Squares Regression line for the input baseline data including, but not limited to, age, workout duration and muscle flexibility (act 304). The best fit line may be determined by logistic regression or other well-known techniques. In some cases a Linear Least-Squares Regression line may not be appropriate. In such cases, a non-linear least-squares regression curve may be used to achieve the most appropriate fit.

Next, a baseline flexibility quotient may be calculated (act 306). One method for calculating the baseline flexibility quotient according to some embodiments may involve solving for p in an equation of a form $$\ln\left(\frac{p}{1-p}\right) =$$

-continued $$C_0 + (C_1 \times age) + (C_2 \times workout\_duration) + (C_3 \times muscle\_flexibility),$$

where age is an age of an individual, workout_duration is a time in minutes for a workout, and muscle_flexibility is a measurement of muscle flexibility, which may have an inclusive range between 0% and 100%. $C_0$, $C_1$, $C_2$ and $C_3$ are constants that may be derived by using binary regression or other well-known techniques. In other embodiments, additional parameters may be included in the above formula. Solving the above equation for p results in:

$$p = \frac{e^{C_0+(C_1 \times age)+(C_2 \times workout\_duration)+(C_3 \times muscle\_flexibility)}}{(1 + e^{C_0+(C_1 \times age)+(C_2 \times workout\_duration)+(C_3 \times muscle\_flexibility)})}.$$

A flexibility quotient may then be set to p (act 308). For example, assume that $C_0$ is 11.057, $C_1$ is −5.45, $C_2$ is 0.56, $C_3$ is 0.85551, age is 28, workout duration is 100 minutes and muscle flexibility is 100%. The above equation now becomes $$p = \frac{e^{11.057+(-5.45 \times 28)+(0.56 \times 100)+(0.85551 \times 100)}}{(1 + e^{11.057+(-5.45 \times 28)+(0.56 \times 100)+(0.85551 \times 100)})} =$$

$$\frac{e^{0.008}}{1 + e^{0.008}} = \frac{1.008032}{2.008032} = 0.502.$$

Thus, the flexibility quotient is 0.502.

Although the example process of FIG. 3 describes computing device 104 as performing the process, in some embodiments, the input baseline data may be provided by computing device 104 to server 110, which may perform acts 304-308 and may return the baseline flexibility quotient to computing device 104.

Figure 4:
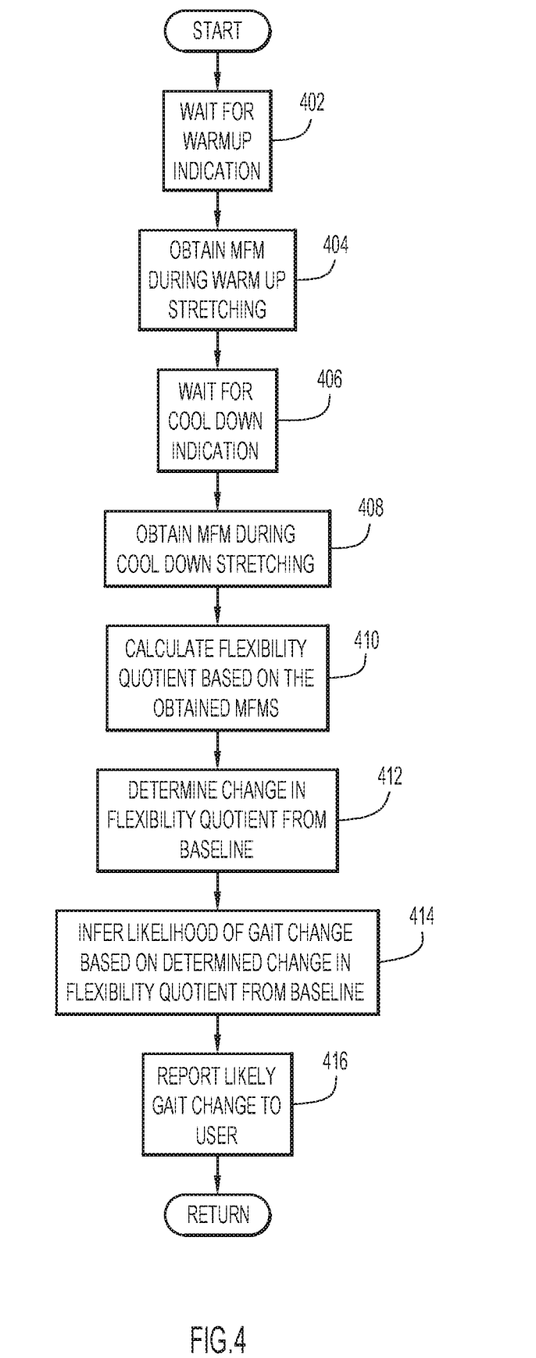
FIG. 4 is a flowchart showing example processing for inferring a change in gait based on a determined change in a flexibility quotient from a baseline flexibility quotient according to embodiments of the invention.

FIG. 4 is a flowchart of a process for obtaining a muscle flexibility measurement, calculating a flexibility quotient, and inferring or predicting a likelihood of a gait change based on an amount of change in the flexibility quotient from the baseline flexibility quotient. The process may begin with computing device 104 receiving a warmup indication regarding an individual performing warmup stretching exercises (act 402). The indication may be provided by an action of the individual including, but not limited to, pressing or touching a hard or soft button of computing device 104, typing a specific command, speaking a voice command, or other action. Next, computing device 104 may obtain a first muscle flexibility measurement during the warmup stretching exercises (act 404). If computing device 104 is a small device such as, for example, a smart phone having at least one sensor, the smartphone may be attached to a specific body part such as, for example, an upper portion or a lower portion of a leg of the individual or other body part, and may measure a change in angle of the specific body part to which computing device 104 is attached during the stretching exercises. Alternatively, supplemental sensing device 106 may be attached to the specific body part and may measure a change in angle of the specific body part to which supplemental sensing device 106 is attached during the stretching exercises and may report the change in angle to computing device 104, which obtains the muscle flexibility measurement based on the change in angle.

Computing device 104 may then wait for a cooldown indication, which may be provided by the individual via one of a number of different methods, including any of the methods discussed above with respect to providing a warmup indication (act 406). Computing device 104 may then obtain a second muscle flexibility measurement during cooldown stretching exercises by the individual (act 408). The second muscle flexibility measurement may be obtained in a same manner as the first muscle flexibility measurement. A muscle flexibility measurement to be used when calculating a flexibility quotient may be calculated based on the first muscle flexibility measurement and the second muscle flexibility measurement. According to some embodiments, the muscle flexibility measurement may be an average value of the first muscle flexibility measurement and the second muscle flexibility measurement. The flexibility quotient may then be calculated based on using the provided baseline data, the muscle flexibility measurement, and a formula such as, for example, a formula previously described, and solving for p (act 410).

Next, a change in the flexibility quotient from the baseline flexibility quotient may be determined (act 412). Based on the change in the flexibility quotient, with respect to the baseline flexibility quotient, a likelihood of a gait change may be inferred (act 414) and a likely gait change may be reported to the individual via a display screen of computing device 104, or via other methods, which may include, but not be limited to, computer generated speech, an email message, and a text message (act 416). The process may then be completed.

Gait may be classified into a number of different types. For example, types of gait may include, but not be limited to, normal, magnetic, high-stepping, and slapping. Normal gait is characterized by an individual's heel hitting a floor first and the individual's foot rotating forward with the toes being a last portion of the foot to touch the floor. Magnetic gait can be characterized as the individual's feet seemingly attached to the floor as if by a magnet. Magnetic gait can be visualized in terms of a powerful magnet being forcefully pulled from a steel plate. High-stepping gait is characterized by foot drop due to loss of dorsiflexion. An individual with a high-stepping gait has a foot that hangs with the toes pointing down, causing the toes to scrape the ground while walking, thereby requiring the individual to lift his or her leg higher than normal when walking. Slapping gait is characterized by the individual's foot slapping the floor with each step. According to some embodiments, a gait diagnosis may be suggested based on increased or decreased muscle flexibility of a specific body part.

TABLE 1

Example recommendations based on flexibility quotient change from a baseline

| Flexibility Quotient | Comments/Recommendations |
| --- | --- |
| 0.5 | Baseline Measurement |
| 0.33 | Improved Flexibility, recommend a gait measurement recheck. |
| 0.75 | Moderate loss in flexibility from baseline. Potential change from high stepping to slapping gait. |
| 0.45 | Baseline Measurement |
| 0.49 | Minimal flexibility quotient change, no recommendations. |
| 0.69 | Moderate loss in flexibility from baseline, suggest a new gait measurement, potential change from slapping to sensory ataxia. |

Table 1 shows some sample recommendations, comments and gait diagnoses based on a change in flexibility quotient from a baseline flexibility quotient. An increase in the flexibility quotient indicates a decrease in flexibility and a decrease in the flexibility quotient indicates an improvement in flexibility. For example, a top row of Table 1 shows a baseline flexibility quotient of 0.5. A next row shows a flexibility quotient of 0.33, which when compared to the baseline measurement of 0.5 shows improved flexibility. When the change indicates improved flexibility, a gate measurement recheck may be recommended. A third row shows a flexibility quotient of 0.75, which indicates a moderate loss in flexibility from the baseline flexibility quotient of 0.5. When the change indicates a moderate loss in flexibility (e.g., an increase of at least 0.20 in the flexibility quotient), a new gait measurement may be recommended and a possible change in gait may be indicated. For example, if the baseline gate is high-stepping, a potential change from a high-stepping gait to a slapping gait may be indicated and a notification may be provided. A fourth row shows a second baseline measurement having a flexibility quotient of 0.45. A fifth row shows a flexibility quotient of 0.49, which is a minimal flexibility quotient change from the baseline flexibility quotient of 0.45. When a minimal change in the flexibility is indicated such as, for example, an increase or decrease of 0.04 in the flexibility quotient, no recommendations may be provided. A sixth row shows a flexibility quotient of 0.69, which when compared to the second baseline measurement of 0.45 shows a moderate loss in flexibility. When a moderate loss in flexibility is indicated (e.g., an increase in the flexibility quotient of at least 0.20), a new gait measurement may be recommended and a potential change in gait may be indicated. For example, if the baseline gait is a slapping gait, a gait change to sensory ataxia (loss of coordination) may be indicated and a notice may be provided. Similarly, when a moderate improvement is flexibility is indicated, a gait measurement recheck may be suggested and a possible change in gate may be indicated.

Figure 5:
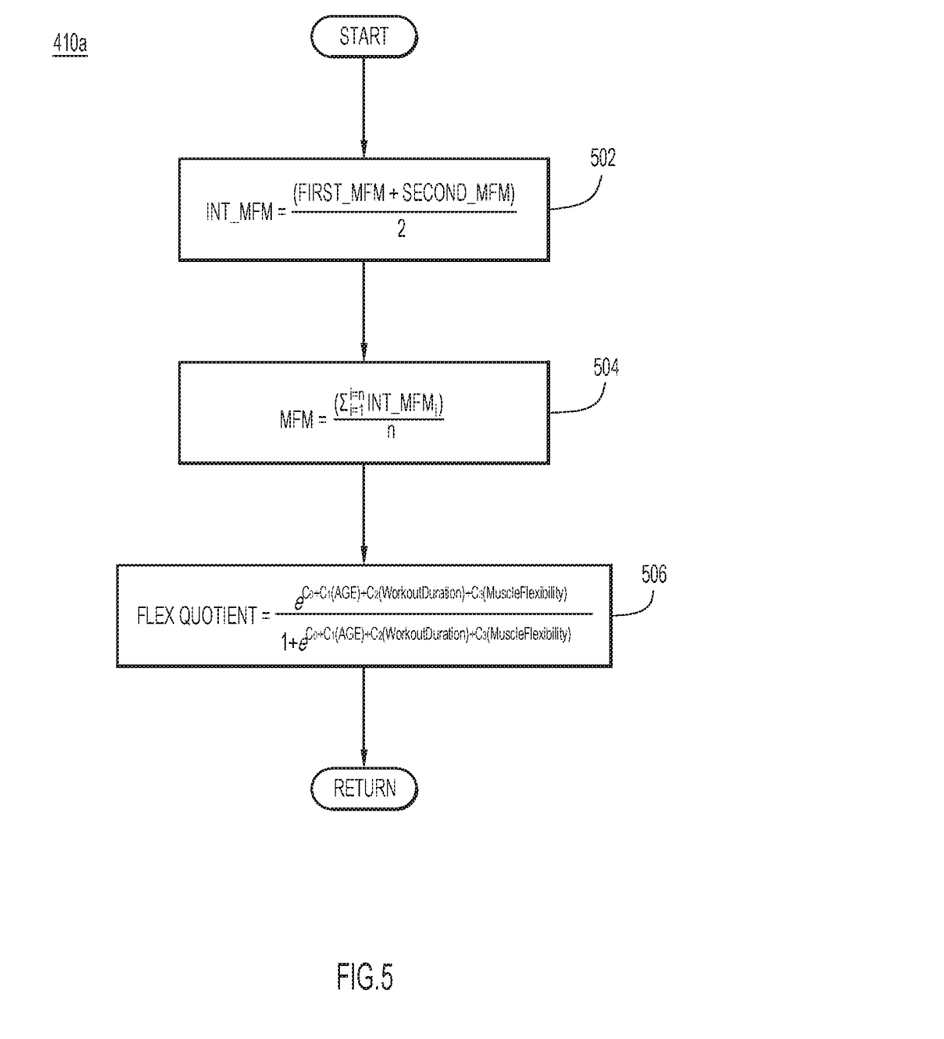
FIG. 5 is a flowchart of an example process for calculating a muscle flexibility measurement based on a moving average of a given number of previous muscle flexibility measurements according to embodiments of the invention.

Because an incorrect muscle flexibility measurement will result in an incorrect flexibility quotient, which may further result in an incorrect comment, suggestion, or diagnosis, it may be desirable to smooth out an effect of an incorrect muscle flexibility measurement. FIG. 5 is a flowchart of an example process for performing an alternative method 410a with respect to act 410 of FIG. 4, in which the effect of an incorrect flexibility measurement may become insignificant. In embodiments in which alternative method 410a is performed, an intermediate muscle flexibility measurement (INT_MFM) may be calculated as an average of a first muscle flexibility measurement and a second muscle flexibility measurement, respectively, measured during warmup stretching exercises and cooldown stretching exercises (act 502). Next, an effect of the calculated intermediate muscle flexibility measurement (INT_MFM) may be spread over a given number, n, of previously calculated intermediate muscle flexibility measurements (act 504). Thus, for example, if n is 10, then a sum of the intermediate muscle flexibility measurement, just calculated, and a previous n−1 intermediate muscle flexibility measurements may be divided by n to produce a muscle flexibility measurement to be used when calculating a flexibility quotient (act 506). That is, the muscle flexibility measurement for use in calculating the flexibility quotient is a moving average of a last n calculated muscle flexibility measurements. If there are fewer than n previous intermediate muscle flexibility measurements, then fewer than n previous intermediate muscle flexibility measurements may be used when calculating a flexibility quotient.

Figure 6:
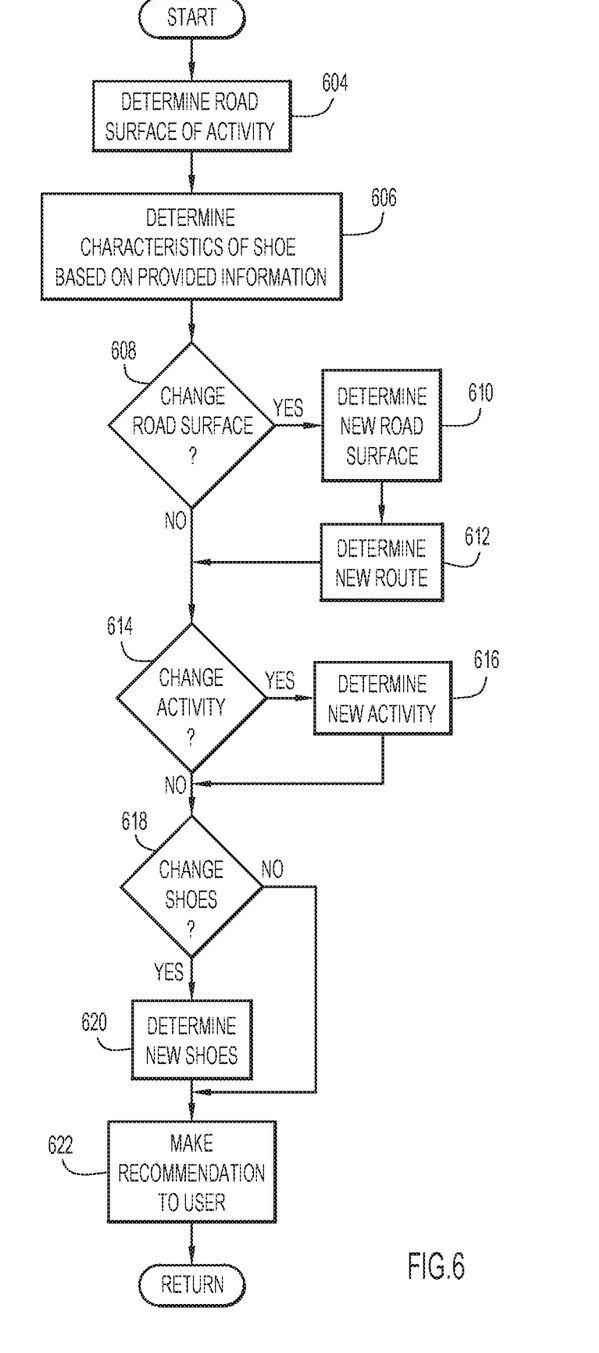
FIG. 6 is a flowchart of an example process of an exercise application, according to embodiments of the invention, for determining a new training route, a new activity, and/or a new change of shoes and recommending the same to a user.

FIG. 6 is a flowchart illustrating an example process that may be performed according to an embodiment. The process may be performed by a fitness application executing on computing device 104 after the process of FIG. 4 is executed and a likely gait change is inferred. The process of FIG. 4 may persist information in a database accessible by the fitness application. The information may include, but not be limited to, the baseline flexibility quotient, the recently calculated flexibility quotient, and the inferred likelihood of the gait change. In this embodiment, additional information may be provided such as, for example, a brand and model of a shoe used by the individual. According to some embodiments, the additional information may be input through computing device 104 and persisted to a database accessible by the fitness application. The process may begin by determining a type of road surface on which the individual recently performed an activity including, but not limited to, running and walking (act 604). Computing device 104 and/or server 110 may determine the type of road surface based on obtained location information while the activity was being performed. The location information may be provided via use of a Global Positioning System (GPS), Wi-Fi, or other location determining mechanism. Alternatively, the individual who performed the activity may input information regarding a type of road surface into computing device 104 via an input means such as, for example, a touchpad, a keyboard, a microphone, or other input device.

Next, computing device 104 may determine characteristics of a shoe based on provided information (act 606). The provided information may include, but not be limited to, a brand and a model of the shoe.

Computing device 104, or a combination of server 110 and computing device 104, may determine whether a change in road surface should be recommended based on an amount of change of the flexibility quotient from the baseline flexibility quotient (act 608). If a change in road surface is determined, then a new type of road surface for the activity may be determined (act 610). For example, if the individual was running on a concrete surface and the flexibility quotient indicates a significant loss in flexibility with respect to the baseline flexibility quotient (in some embodiments, a flexibility quotient of at least 0.25 (or other suitable amount) higher than the baseline flexibility quotient may be considered significant), then the new road surface type may be determined to be grass. Computing device 104, or the combination of server 110 and computing device 104, may determine a new route for the activity using surrounding location information (act 612). For example, if the new road surface is a grass surface, then the new route will have grass as the road surface.

Next, a determination may be made regarding whether a change in activity should be made based on the amount of change of the flexibility quotient from the baseline flexibility quotient (act 614). As an example, if the amount of the change of the flexibility quotient indicates a significant loss of flexibility and the current activity is running, then a new activity of walking may be determined (act 616).

According to some embodiments, an individual may input the type of activity via computing device 104, which may persist the type of activity to a database accessible to a fitness application. Alternatively, computing device 104 and/or server 110 may determine a distance travelled during the activity, such as an outdoor activity. Given a workout duration and the distance traveled, computing device 104 and/or server 110 may determine a type of activity performed such as, for example, walking running, or cycling.

Next, a determination may be made regarding whether a change of shoes should be recommended (act 618) based on a determined change of the flexibility quotient from the baseline flexibility quotient. If a change of shoes is to be recommended, then computing device 104 or server 110 may access websites of shoe manufacturers to access detailed shoe information to determine a brand and a model shoe to recommend based on the detailed shoe information, the additional provided information, and the determined difference in the flexibility quotient from the baseline flexibility quotient (act 620). Other information may be provided and used for determining a shoe to recommend such as, for example, a gait type and pronation, if known.

Recommendations regarding a new route, or road surface, a change in activity, and a new type of shoe may then be provided to the individual via a display of computing device 104, email, text message, computer-generated speech, or other methods (act 622).

In some embodiments, computing device 104 may monitor a distance traveled during workouts, and if a downward or upward trend is detected with respect to the distance traveled and a corresponding downward or upward trend in flexibility is also detected via changes in the flexibility quotient, then computing device 104 may dynamically alter a route for a workout while the workout is taking place. For example, if an individual jogs and his or her distance traveled has been steadily declining and the flexibility quotient has been steadily increasing, indicating a decrease in flexibility, then a running route may be dynamically changed from a route having a concrete surface to a route having a grass surface. Further, if the jogging individual's distance traveled has been steadily increasing and the flexibility quotient has been steadily decreasing, indicating an increase in flexibility, then the running route may be dynamically changed from a route with a grass surface to a route with a concrete surface.

It will be appreciated that the embodiments described above and illustrated in the drawings represent only a few of the many ways of implementing various embodiments for monitoring flexibility and diagnosing changes in gait.

The environment of the present invention embodiments may include any number of computer or other processing systems and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., browser software, communications software, server software). These systems may include any types of monitors and input devices (e.g., keyboard, mouse, voice recognition, etc.) to enter and/or view information.

It is to be understood that the software of the present invention embodiments may be implemented in any desired computer language and could be developed by one of ordinary skill in the computer arts based on the functional descriptions contained in the specification and flowcharts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various computing systems, and/or any other intermediary processing devices. The software and/or algorithms described above and illustrated in the flowcharts may be modified in any manner that accomplishes the functions described herein. In addition, the functions in the flowcharts or description may be performed in any order that accomplishes a desired operation.

The software of the present invention embodiments may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information. The database system may be implemented by any number of any conventional or other databases, data stores or storage structures to store information. The database system may be included within or coupled to server and/or client systems. The database systems and/or storage structures may be remote from or local to a computer or other processing systems, and may store any desired data.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special-purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the FIGS. illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the FIGS. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The invention claimed is:

1. A machine-implemented method for measuring and analyzing muscle flexibility to infer a change in gait, the method being performed by at least one computing device and comprising:
   receiving measurements from at least one sensor of a device attached to a leg of a user, wherein the measurements include a change in an angle of the leg during warmup and cooldown stretching exercises;
   determining muscle flexibility measurements based on the measured change in angle of the leg;
   calculating a flexibility quotient based on:
      information including the muscle flexibility measurements, and baseline data including user information, a type of activity, and a workout duration; and
      coefficients determined from a regression analysis for a best fit line for the information;
   determining a change in flexibility based on a difference between the calculated flexibility quotient and a baseline flexibility quotient;
   inferring the change in gait based on the determined change in flexibility;
   reporting the inferred change in gait to the user;
   determining a type of road surface based on location information obtained while an activity is being performed; and
   executing a fitness application for an outdoor activity, wherein the fitness application recommends a different training route having a different type of road surface than the determined type of road surface based on the determined change in flexibility and surrounding location information.

2. The machine-implemented method of claim 1, wherein the calculating the flexibility quotient further comprises:
   calculating an intermediate flexibility measurement based on an average value of a first muscle flexibility measurement during the warmup stretching exercises and a second muscle flexibility measurement during the cooldown stretching exercises; and
   calculating the flexibility quotient using a moving average of the calculated intermediate flexibility measurement and a given number of previously calculated intermediate flexibility measurements.

3. The machine-implemented method of claim 1, wherein the baseline data further includes a current gait type, a pronation type and a baseline muscle flexibility measurement.

4. The machine-implemented method of claim 1,
   further comprising suggesting a likely gait diagnosis to the user based on a change in the muscle flexibility measurements related to the leg.

5. The machine-implemented method of claim 1, further comprising:
   obtaining information regarding a type of shoe used, wherein the fitness application recommends a different type of shoe based on the determined change in flexibility.

6. The machine-implemented method of claim 5, further comprising:
   periodically determining a location of the user;
   determining a type of the performed activity based on a rate of change with respect to the determined location of the user.

7. The machine-implemented method of claim 1, wherein:
   the device attached to the leg of the user is a separate device from the at least one computing device; and
   the at least one computing device resides in a smartphone that communicates wirelessly with the separate device to receive the measurements from the at least one sensor.

8. A system for inferring a change in gait from a baseline, the system comprising:
   at least one processor; and
   a memory connected to the at least one processor, wherein the at least one processor is configured to perform:
      receiving measurements from a device attached to a leg of a user and having at least one sensor, wherein the measurements include a change in an angle of the leg during warmup and cooldown stretching exercises;
      determining muscle flexibility measurements based on the measured change in angle of the leg;
      calculating a flexibility quotient based on:
         information including the muscle flexibility measurements, and baseline data including user information, a type of activity, and a workout duration; and
         coefficients determined from a regression analysis for a best fit line for the information;
      determining a change in flexibility based on a difference between the calculated flexibility quotient and a baseline flexibility quotient;
      inferring the change in gait based on the determined change in flexibility;
      reporting the inferred change in gait to the user;
      determining a type of road surface based on location information obtained while an activity is being performed; and
      executing a fitness application for an outdoor activity, wherein the fitness application recommends a different training route having a different type of road surface than the determined type of road surface based on the determined change in flexibility and surrounding location information.

9. The system of claim 8, wherein the calculating the flexibility quotient further comprises:
   calculating an intermediate flexibility measurement based on an average value of a first muscle flexibility measurement during the warmup stretching exercises and a second muscle flexibility measurement during the cooldown stretching exercises; and
   calculating the flexibility quotient using a moving average of the calculated intermediate flexibility measurement and a given number of previously calculated intermediate flexibility measurements.

10. The system of claim 8, wherein the baseline data further includes a current gait type, a pronation type and a baseline muscle flexibility measurement.

11. The system of claim 8, wherein
   the at least one processor is further configured to perform:
      suggesting a likely gait diagnosis to the user based on a change in the muscle flexibility measurements related to the leg.

12. The system of claim 8, wherein the at least one processor is further configured to perform:
   obtaining information regarding a type of shoe used, wherein the fitness application recommends a different type of shoe based on the determined change in flexibility.

13. The system of claim 12, wherein the at least one processor is further configured to perform:

periodically determining a location of the user;
determining a type of the performed activity based on a rate of change with respect to the determined location of the user.

14. The system of claim 8, wherein:
the at least one processor resides in a smartphone that communicates wirelessly with the device attached to the leg of the user to receive the measurements from the device.

15. A computer program product comprising at least one computer readable storage medium having computer readable program code embodied therewith for execution on at least one processor, the computer readable program code being configured to be executed by the at least one processor to perform:
receiving measurements from a device attached to a leg of a user and having at least one sensor, wherein the measurements include a change in an angle of the leg during warmup and cooldown stretching exercises;
determining muscle flexibility measurements based on the measured change in angle of the leg;
calculating a flexibility quotient based on:
information including the muscle flexibility measurements, and baseline data including user information, a type of activity, and a workout duration; and
coefficients determined from a regression analysis for a best fit line for the information;
determining a change in flexibility based on a difference between the calculated flexibility quotient and a baseline flexibility quotient;
inferring a change in gait based on the determined change in flexibility;
reporting the inferred change in gait to the user;
determining a type of road surface based on location information obtained while an activity is being performed; and
executing a fitness application for an outdoor activity, wherein the fitness application recommends a different training route having a different type of road surface than the determined type of road surface based on the determined change in flexibility and surrounding location information.

16. The computer program product of claim 15, wherein the calculating the flexibility quotient further comprises:
calculating an intermediate flexibility measurement based on an average value of a first muscle flexibility measurement during the warmup stretching exercises and a second muscle flexibility measurement during the cooldown stretching exercises; and
calculating the flexibility quotient using a moving average of the calculated intermediate flexibility measurement and a given number of previously calculated intermediate flexibility measurements.

17. The computer program product of claim 15, wherein the baseline data further includes a current gait type, a pronation type and a baseline muscle flexibility measurement.

18. The computer program product of claim 15, wherein the computer readable program code is further configured to be executed by the at least one processor to perform suggesting a likely gait diagnosis to the user based on a change in the muscle flexibility measurements related to the leg.

19. The computer program product of claim 15, wherein the computer readable program code is further configured to be executed by the at least one processor to perform:
obtaining information regarding a type of shoe used, wherein the fitness application recommends a different type of shoe based on the determined change in flexibility.

20. The computer program product of claim 15, wherein the device attached to the leg of the user is a smartphone.

* * * * *